United States Patent
Maeda

(10) Patent No.: US 8,222,452 B2
(45) Date of Patent: Jul. 17, 2012

(54) METHOD FOR PRODUCING OPTICALLY ACTIVE AMINES

(75) Inventor: Sadayuki Maeda, Kyoto (JP)

(73) Assignee: Hamari Chemicals, Ltd., Osaka (JP)

( * ) Notice: Subject to any disclaimer, the term of this patent is extended or adjusted under 35 U.S.C. 154(b) by 178 days.

(21) Appl. No.: 12/452,402

(22) PCT Filed: Jun. 30, 2008

(86) PCT No.: PCT/JP2008/061809
§ 371 (c)(1),
(2), (4) Date: Feb. 18, 2010

(87) PCT Pub. No.: WO2009/005024
PCT Pub. Date: Jan. 8, 2009

(65) Prior Publication Data
US 2010/0160636 A1    Jun. 24, 2010

(30) Foreign Application Priority Data
Jul. 3, 2007    (JP) .................................. 2007-175278

(51) Int. Cl.
*C07C 303/00*    (2006.01)
*C07C 211/00*    (2006.01)
(52) U.S. Cl. .......................................... 564/86; 564/463
(58) Field of Classification Search .................. 564/463, 564/86
See application file for complete search history.

(56) References Cited

U.S. PATENT DOCUMENTS

| 6,184,381 B1 | 2/2001 | Ikariya et al. |
| 7,230,134 B2 * | 6/2007 | Borner et al. .................. 564/398 |
| 2002/0095056 A1 | 7/2002 | Cobley et al. |
| 2004/0267051 A1 | 12/2004 | Boerner et al. |

FOREIGN PATENT DOCUMENTS

CZ    293 922    8/2004

OTHER PUBLICATIONS

Nugent et al. Adv. Synth. Catal. 2010, 352, 753-819.*
Alcon et al. Journal of Organometallic Chemistry 634 (2001) 25-33.*
Lipkowitz et al. J. Am. Chem. Soc. 2002, 124, 14255-14267.*
English translation of International Preliminary Report on Patentability.
W. Hoffmuller et al., "Metallkomplexe mit biologisch wichtigen Liganden. XCV[1] $n^5$-Pentamethylcyclopentadienyl-Rhodium-, Iridium-, ($n^6$-Benzol)-Buthenium- und Phosphan-Palladium-Komplexe von Prolinmethylester und Prolinamid", Z. Anorg. Allg. Chem. 623, pp. 1903-1911, 1997.
International Search Report issued Aug. 12, 2008 in International (PCT) Application No. PCT/JP2008/061809.
Supplementary European Search Report dated Jul. 15, 2011 in European Application No. 08790722.6.

* cited by examiner

*Primary Examiner* — Nizal Chandrakumar
(74) *Attorney, Agent, or Firm* — Wenderoth, Lind & Ponack, L.L.P.

(57) ABSTRACT

The present invention provides a method for producing chiral amines, comprising asymmetric transfer hydrogenation of imine compounds in the presence of a hydrogen donor compound and an iridium(III) complex having a chiral prolinamide compound as a ligand. The present invention is useful for production of chiral amines in an efficient manner in terms of their optical and chemical yields.

7 Claims, No Drawings

METHOD FOR PRODUCING OPTICALLY ACTIVE AMINES

This application is a U.S. national stage of International Application No. PCT/JP2008/061809 filed Jun. 30, 2008.

TECHNICAL FIELD

The present invention relates to a novel method for producing optically active amines.

BACKGROUND ART

Optically active amines (hereinafter sometimes referred to as chiral amines) are compounds of importance extensively used in the fields of fine chemicals, pharmaceuticals, agrochemicals and the like.

As a method for producing optically active amines from ketone and amine, the followings are known:
a method in which ketone and amine are subjected to reductive amination for production of an amine compound, and the amine compound is optically resolved using an optically resolving agent (for example, chiral camphorsulfonic acid etc.), and
a method in which ketone and optically active α-methylbenzylamine are subjected to reductive amination for production of an amine compound having a benzyl group, and then the amine compound is decomposed into an optically active amine. For example, the patent literature 1 discloses a method which involves hydrogenating 5-acetonyl-2-methoxybenzenesulfonamide and (R)-(+)-α-methylbenzylamine in the presence of a platinum catalyst (platinum oxide) into 2R,1R-methoxy-5-[2-(1-methylbenzylamino)propyl]benzenesulfonamide, and then subjecting the resulting compound to catalytic reduction to obtain (R)-methoxy-5-(2-aminopropyl)benzenesulfonamide.

As a more advantageous method for producing optically active amines, a method involving use of a chiral metal catalyst for asymmetric reduction of imine compounds obtained from ketone and amine is known. For example, the patent literature 2 discloses a method for producing optically active amines, the method involving asymmetric transfer hydrogenation of ketone and amine in the presence of a hydrogen donor and a catalyst. In this literature, as the catalyst, there is used, for example, a metal catalyst produced by reaction of a chiral or achiral, phosphine or diphosphine ligand with a metal pre-complex (for example, [(S—BINAP)RuCl$_2$(DMF)$_x$], [(R-TolBINAP)RuCl$_2$(DMF)$_x$], [Ir(C$_8$H$_{12}$)Cl]$_2$, [Ir(C$_8$H$_{14}$)$_2$Cl]$_2$+R-TolBINAP, etc.). Further, the patent literature 3 discloses a method for producing optically active amines, the method involving asymmetric transfer hydrogenation of imine compounds in the presence of a hydrogen donor and a chiral ruthenium complex represented by the following formula:

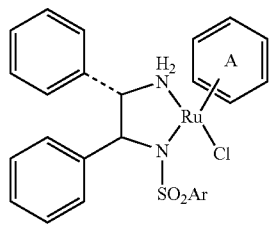

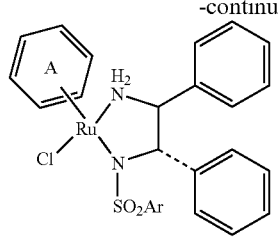

(wherein the ring A represents benzene or p-cymene, and Ar represents tolyl, 2,4,6-trimethylphenyl or 1-naphthyl).

Furthermore, the nonpatent literature 1 discloses a method for producing optically active amines, the method involving asymmetric transfer hydrogenation of ketone and ammonium formate in the presence of an iridium catalyst (for example, a catalyst formed of (1R,2R)-1,2-diphenyl-1,2-ethylenediamine and [Ir(C$_8$H$_{14}$)$_2$Cl]$_2$/2 or [Ir(C$_5$Me$_5$)Cl$_2$]$_2$/2).

Such conventional methods, however, are not necessarily satisfying. For example, the method of the nonpatent literature 1, probably due to relatively high temperature of 60 to 85° C. required as its reaction condition, has a disadvantage that besides amine compounds, large amounts of byproducts such as alcohol compounds and N-formylamine compounds are obtained. Moreover, it is generally difficult to obtain good optical yields in the case of simple chain ketones, in which each of the carbon atoms adjacent to the carbonyl group constitutes an alkyl group or the like (nonpatent literatures 1 and 2).

Patent Literature 1: JP-B 6-6565
Patent Literature 2: JP-A 2004-537588
Patent Literature 3: WO 97/20789 pamphlet
Non Patent Literature 1: Angew. Chem. Int. Ed, 2003, 42, 5472-5474
Non Patent Literature 2: Angew. Chem. Int. Ed, 2001, 40, 3425-3427

SUMMARY OF INVENTION

Problem to be Solved by the Invention

An object of the present invention is to provide a method for producing optically active amines in a more highly selective manner in terms of their optical and chemical yields by asymmetric transfer hydrogenation of, under mild reaction conditions, amines and a wide range of ketones including simple chain ketones, which do not produce good results in conventional methods.

Means for Solving the Problem

The present inventors conducted extensive research to achieve the above-mentioned object. As a result, they reached the following finding: objective optically active amines can be obtained in a simple and highly selective manner by a method in which an imine compound produced from ketone and amine, or more simply, an aminoalcohol titanium complex obtained by treating ketone and amine with titanium alkoxide is subjected to asymmetric transfer hydrogenation using, as a catalyst, an iridium(III) complex having chiral prolinamide as a ligand, in the presence of a hydrogen donor compound. Based on this finding, the present inventors conducted further research and completed the present invention.

Namely, the present invention relates to:

[1] a method for producing a chiral amine represented by the formula [II]:

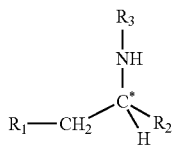

[II]

(wherein $R_1$ represents a hydrogen atom, an optionally substituted alkyl group, an optionally substituted aryl group, an optionally substituted aralkyl group, an optionally substituted cycloalkyl group or an optionally substituted heteroaryl group, and $R_2$ represents an optionally substituted alkyl group, an optionally substituted aralkyl group, an optionally substituted cycloalkyl group, a carboxyl group, an esterified carboxyl group, a cyano group or an amide group, or $R_1$ and $R_2$ together with the adjacent carbon atoms may form a ring by binding to each other at the ends thereof;

$R_3$ represents a hydrogen atom, an optionally substituted alkyl group, an optionally substituted aryl group, an optionally substituted aralkyl group, an optionally substituted heteroaryl group or an optionally substituted cycloalkyl group, or $R_2$ and $R_3$ together with the adjacent group —NH—C— may form a nitrogen containing heterocycle optionally having a substituent; and the symbol "*" represents a chiral carbon atom), comprising subjecting an imine compound represented by the formula [I]:

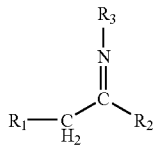

[I]

(wherein $R_1$, $R_2$ and $R_3$ have the same meanings as defined above, or $R_2$ and $R_3$ together with the adjacent group —N=C— may form a nitrogen containing heterocycle optionally having a substituent)

to asymmetric transfer hydrogenation in the presence of a hydrogen donor compound and an iridium(III) complex having a chiral prolinamide compound as a ligand,

[2] a method for producing a chiral amine represented by the formula [VII]:

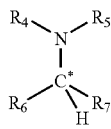

[VII]

(wherein $R_4$ and $R_5$ independently represent a hydrogen atom, an optionally substituted alkyl group, an optionally substituted aryl group, an optionally substituted aralkyl group, an optionally substituted heteroaryl group or an optionally substituted cycloalkyl group, or $R_4$ and $R_5$ together with the adjacent nitrogen atom may form a ring by binding to each other at the ends thereof;

$R_6$, which is different from $R_7$, represents an optionally substituted alkyl group, an optionally substituted aryl group, an optionally substituted aralkyl group, an optionally substituted cycloalkyl group or an optionally substituted heteroaryl group, and $R_7$ represents an optionally substituted alkyl group, an optionally substituted aryl group, an optionally substituted aralkyl group, an optionally substituted heteroaryl group, an optionally substituted cycloalkyl group, a carboxyl group, an esterified carboxyl group, a cyano group or an amide group, or $R_6$ and $R_7$ together with the adjacent carbon atom may form a ring by binding to each other at the ends thereof; and the symbol "*" represents a chiral carbon atom), comprising reacting an amine represented by the formula [III]:

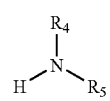

[III]

(wherein $R_4$ and $R_5$ have the same meanings as defined above) and a ketone represented by the formula [IV]:

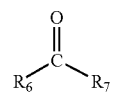

[IV]

(wherein $R_6$ and $R_7$ have the same meanings as defined above) with a metal compound represented by the formula [V]:

$$MX_n \qquad [V]$$

(wherein M represents an atom selected from the group consisting of boron, aluminum, zinc, titanium and zirconium, n represents the valence number of M, and X represents an alkoxy group, an aryloxy group, an acyloxy group, a sulfoxy group, a trifluoromethanesulfoxy group or halogen)

to produce a metal-containing aminoalcohol compound represented by the formula [VI]:

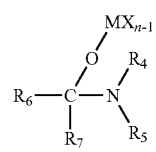

[VI]

(wherein $R_4$, $R_5$, $R_6$, $R_7$, M, n and X have the same meanings as defined above), and then subjecting the metal-containing aminoalcohol compound to asymmetric transfer hydrogenation in the presence of a hydrogen donor compound and an iridium(III) complex having a chiral prolinamide compound as a ligand,

[3] the method according to the above [1] or [2], wherein the chiral prolinamide compound is a compound represented by the formula [VIII]:

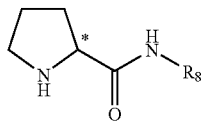

[VIII]

(wherein $R_8$ represents a hydrogen atom, an optionally substituted alkyl group, an optionally substituted aryl group, an optionally substituted heteroaryl group, an optionally substituted aralkyl group or an optionally substituted cycloalkyl group, and the symbol "*" represents a chiral carbon atom),

[4] the method according to the above [3], wherein the chiral prolinamide compound represented by the formula [VIII] is (R)-prolinamide or (S)-prolinamide,

[5] the method according to the above [3], wherein the chiral prolinamide compound represented by the formula [VIII] is (R)-proline heteroaryl amide or (S)-proline heteroaryl amide,

[6] the method according to the above [3], wherein the chiral prolinamide compound represented by the formula [VIII] is (R)—N-(6-quinolinyl)-2-pyrrolidinecarboxamide or (S)—N-(6-quinolinyl)-2-pyrrolidinecarboxamide,

[7] the method according to the above [3], wherein the chiral prolinamide compound represented by the formula [VIII] is (R)—N-(2-methoxy-3-dibenzofuranyl)-2-pyrrolidinecarboxamide or (S)—N-(2-methoxy-3-dibenzofuranyl)-2-pyrrolidinecarboxamide,

[8] the method according to the above [1] or [2], wherein the iridium(III) complex having a chiral prolinamide compound as a ligand is an (S)- or (R)-chloro[(1,2,3,4-η)-pentamethyl-2,4-cyclopentadien-1-yl][N-(2-methoxy-3-dibenzofuranyl)-2-pyrrolidinecarboxamidato-κN1,κN2]iridium(III) catalyst, an (S)- or (R)-chloro[(1,2,3,4-η)-pentamethyl-2,4-cyclopentadien-1-yl](N-6-quinolinyl-2-pyrrolidinecarboxamidato-κN1,κN2)iridium(III) catalyst, or an (S)- or (R)-chloro[(1,2,3,4-η)-pentamethyl-2,4-cyclopentadien-1-yl](2-pyrrolidinecarboxamidato-κN1,κN2)iridium(III) catalyst,

[9] the method according to any of the above [1] to [8], wherein the hydrogen donor compound is formic acid,

[10] the method according to the above [2], wherein the metal compound represented by the formula [V] is titanium tetraisopropoxide,

[11] a method for producing tamuslosin represented by the formula [II-a]:

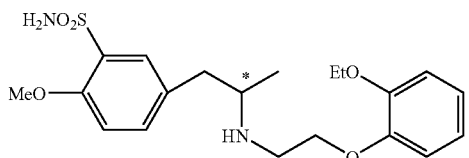

[II-a]

(wherein Me represents a methyl group, Et represents an ethyl group, and the symbol "*" represents a chiral carbon atom), or an acid addition salt thereof, comprising subjecting an imine compound represented by the formula [I-a]:

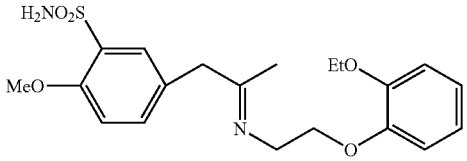

[I-a]

(wherein Me and Et have the same meanings as defined above) to asymmetric transfer hydrogenation in the presence of a hydrogen donor compound and an iridium(III) complex having a chiral prolinamide compound as a ligand, and if desired, converting the resulting product into an acid addition salt thereof, and

[12](S)—N-(2-methoxy-3-dibenzofuranyl)-2-pyrrolidinecarboxamide or (R)—N-(2-methoxy-3-dibenzofuranyl)-2-pyrrolidinecarboxamide Effect of the Invention According to the production method of the present invention, objective chiral amines can be simply produced from a wider range of ketones including simple chain ketones and imine compounds thereof as starting materials in an efficient manner in terms of chemical and optical selectivity.

BEST MODE FOR CARRYING OUT THE INVENTION

According to the present invention, optically active amines can be efficiently produced through the following reaction route (A) or (B).

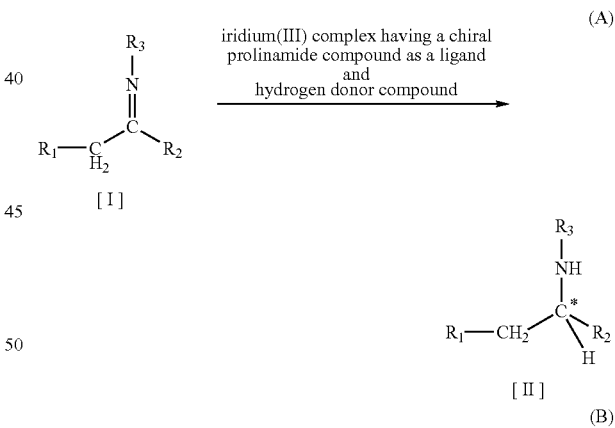

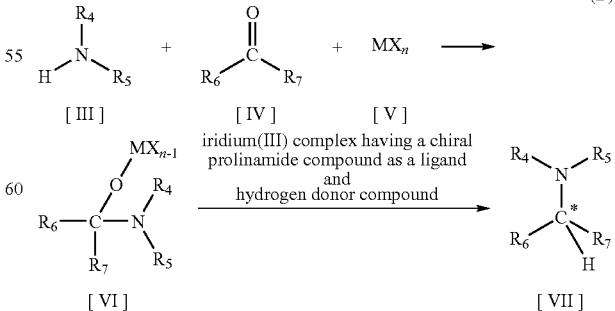

Hereinafter, each step will be explained.

Catalyst Preparation

Examples of the chiral prolinamide compound used as a ligand of the catalyst in the reaction of the present invention include a compound represented by the formula [VIII]:

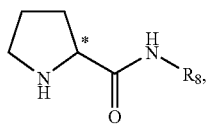

namely, not only non-substituted amide of proline, but also N-substituted amide of proline such as N-alkylamide, N-cycloalkyl amide, N-aryl amide, N-heteroaryl amide, N-aralkyl amide and N-heteroaryl alkylamide of proline. The "alkyl" moiety in the N-alkylamide is preferably a straight or branched alkyl group having 1 to 20 carbon atoms but no chiral carbon atoms. Examples thereof include methyl, ethyl, propyl, isopropyl, butyl, isobutyl, tert-butyl, pentyl, hexyl, heptyl, octyl, nonyl, decyl, dodecyl, pentadecyl, hexadecyl and octadecyl. The "cycloalkyl" moiety in the N-cycloalkyl amide is preferably a cycloalkyl group having 3 to 7 carbon atoms. Examples thereof include cyclopropyl, cyclobutyl, cyclopentyl, cyclohexyl and cycloheptyl. The "aryl" moiety in the N-aryl amide may be, for example, an aromatic hydrocarbon group having 6 to 14 carbon atoms and optionally having a substituent. Examples thereof include phenyl, naphthyl and anthranil. The "heteroaryl" moiety in the N-heteroaryl amide is preferably a heteroaryl group having a hetero atom selected from a nitrogen atom, a sulfur atom and an oxygen atom. Examples thereof include furyl, thienyl, oxazolyl, isoxazolyl, thiazolyl, isothiazolyl, pyrrolyl, imidazolyl, pyrazolyl, pyridyl, pyrimidinyl, pyrazinyl, phthalazinyl, triazinyl, indolyl, isoindolyl, quinolinyl, isoquinolinyl and dibenzofuranyl. The "aralkyl" moiety in the N-aralkyl amide and the "heteroarylalkyl" moiety in the N-heteroaryl alkylamide may be an alkyl group substituted by the "aryl" moiety exemplified above and an alkyl group substituted by the "heteroaryl" moiety exemplified above, respectively. Examples of the alkyl moiety thereof include methyl, ethyl and propyl. There is no limitation on the kind of a substituent in the above "alkyl", "aryl", "heteroaryl", "aralkyl" and "cycloalkyl" moieties (hereinafter referred to as a substituent (A)), unless the substituent interferes the reaction of the present invention. Examples of the substituent include halogens (for example, fluorine, chlorine, bromine, iodine, etc.), straight or branched alkyl groups having 1 to 6 carbon atoms (for example, methyl, ethyl, propyl, isopropyl, butyl, isobutyl, tert-butyl, pentyl, hexyl, etc.), aralkyl groups having 5 to 12 carbon atoms (for example, phenylethyl, phenylpropyl, naphthylmethyl, etc.), straight or branched alkoxy groups having 1 to 6 carbon atoms (for example, methoxy, ethoxy, propoxy, isopropoxy, butoxy, isobutoxy, tert-butoxy, pentyloxy, hexyloxy, etc.), alkyl halide groups (for example, monofluoromethyl, difluoromethyl, trifluoromethyl, difluoroethyl, trifluoroethyl, trichloromethyl, etc.), alkoxy halide groups (for example, fluoromethoxy, difluoromethoxy, trifluoromethoxy, trifluoroethoxy, etc.), a hydroxyl group, a mercapto group, a nitro group, a nitrile group and an alkoxycarbonyl group. In the above-mentioned ligands, (R) or (S)-proline-N-heteroaryl amide is preferred. Inter alia, (R)—N-(6-quinolinyl)-2-pyrrolidinecarboxamide, (S)—N-(6-quinolinyl)-2-pyrrolidinecarboxamide, (R)—N-(2-methoxy-3-dibenzofuranyl)-2-pyrrolidinecarboxamide or (S)—N-(2-methoxy-3-dibenzofuranyl)-2-pyrrolidinecarboxamide is preferred. Non-substituted (R)- and (S)-prolinamides are most advantageous regarding the ease of availability because their commercial products are readily available.

Examples of the iridium(III) complex used together with the ligand, i.e., the chiral prolinamide compound herein include pentamethylcyclopentadienyl iridium(III) chloride dimer, acetylacetonato iridium(III) and tris(norbornadiene)(acetylacetonato)iridium(III). Pentamethylcyclopentadienyl iridium(III) chloride dimer is especially preferred. The catalyst can be easily prepared by dissolving the free base of a chiral prolinamide compound in a solvent, adding thereto an iridium(III) complex and a base (for example, triethylamine etc.), and stirring the mixture under inert gas (for example, argon etc.) atmosphere at room temperature for several minutes to several hours.

In the case where the iridium(III) complex is a dimer, the amount of use of the ligand, i.e., the chiral prolinamide compound is usually about 2 to 3 mol, and preferably about 2 to 2.2 mol per 1 mol of the dimer. The amount of use of the base is preferably an equimolar amount or slight excess relative to the prolinamide compound. The resulting iridium(III) complex having a chiral prolinamide compound as a ligand may be isolated before use, or a catalyst-containing mixture may be added as it is to a reaction mixture for asymmetric reduction.

Compound [I]→Compound [II]

A chiral amine represented by the general formula [II] can be produced by asymmetric transfer hydrogenation, specifically reacting an imine compound represented by the general formula [I] and a hydrogen donor compound in the presence of a catalyst, i.e., an iridium(III) complex having a chiral prolinamide compound as a ligand. In the imine compound represented by the general formula [I] (hereinafter sometimes referred to just as the Compound [I]), the "alkyl" moiety in the optionally substituted alkyl group represented by $R_1$, $R_2$ or $R_3$ is preferably a straight or branched alkyl group having 1 to 20 carbon atoms. Examples thereof include methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl and oxadecyl. The "aryl" moiety in the optionally substituted aryl group represented by $R_1$ or $R_3$ is preferably an aromatic hydrocarbon group having 6 to 14 carbon atoms. Examples thereof include phenyl, naphthyl and anthranil. Examples of the "aralkyl" moiety in the optionally substituted aralkyl group (=aryl alkyl group) represented by $R_1$, $R_2$ or $R_3$ include alkyl groups having 1 to 3 carbon atoms and being substituted by the above-mentioned "aryl" moiety, more specifically, benzyl, phenylethyl, phenylpropyl and naphthylmethyl, for example. Examples of the "heteroaryl" moiety in the optionally substituted heteroaryl group represented by $R_1$ or $R_3$ include furyl, thienyl, oxazolyl, isoxazolyl, thiazolyl, isothiazolyl, pyrrolyl, imidazolyl, pyrazolyl, pyridyl, pyrimidinyl, pyrazinyl, phthalazinyl, triazinyl, indolyl, isoindolyl, quinolinyl, isoquinolinyl and dibenzofuranyl. The "cycloalkyl" moiety in the optionally substituted cycloalkyl group represented by $R_1$, $R_2$ or $R_3$ is preferably a cycloalkyl group having 3 to 7 carbon atoms. Examples thereof include cyclopropyl, cyclobutyl, cyclopentyl, cyclohexyl and cycloheptyl. Examples of the esterified carboxyl group represented by $R_1$ or $R_2$ include alkoxycarbonyl groups (for example, methoxycarbonyl etc.) and aryloxycarbonyl groups (for example, phenoxycarbonyl etc.). Examples of a substituent in the above "alkyl", "aryl", "aralkyl", "heteroaryl" and "cycloalkyl" moieties are the same as those of the substituent (A) described above.

The nitrogen containing heterocycle optionally having a substituent, the heterocycle which $R_2$ and $R_3$ together with the adjacent group —N=C— form by binding to each other may contain, for example, an oxygen atom or sulfur atom in addition to a nitrogen atom as a heterocyclic atom, and is preferably a five-membered or six-membered ring. The five-membered or six-membered ring may be also fused with another ring (for example, an optionally substituted benzene ring etc.).

The nitrogen containing heterocycle is suitably, for example, a heterocycle represented by the following formula [IX]:

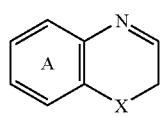

[IX]

(wherein X represents a carbon atom, an oxygen atom or a sulfur atom, and the ring A represents an optionally substituted benzene ring), or the like. More specifically, a 1,4-benzoxazine ring or the like is more suitable. Examples of the substituent are the same as those of the substituent (A) described above.

In the case where the Compound [I] is a compound in which $R_2$ and $R_3$ together with the adjacent group —N=C— form a nitrogen containing heterocycle optionally having a substituent, the reaction proceeds as below in the asymmetric reduction of the present invention.

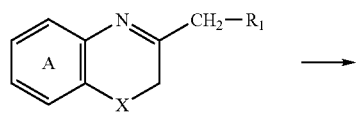

The amount of use of the iridium (III) complex having a chiral prolinamide compound as a ligand is usually about 0.1 to 10 mol %, and preferably about 0.2 to 2 mol % relative to the Compound [I] in the case where the complex is a dimer.

Examples of the hydrogen donor compound include formic acid, triethylammonium formate and 2-propanol. Formic acid is especially preferred. In the case where formic acid is used, it is preferred that a tertiary amine, for example, triethylamine is used together therewith. Examples of the solvent used in this reaction include inert solvents such as acetonitrile, N,N-dimethylformamide, tetrahydrofuran, dimethoxyethane, dichloromethane and alcohols. A formic acid-triethylamine mixture can also be used to serve as the hydrogen donor compound as well as the solvent. The amount of use of the hydrogen donor compound is usually about 1 to 20 mol, and preferably about 4 to 10 mol per 1 mol of the Compound [I]. The amount of use of the solvent is usually 2 to 50 L, and preferably 5 to 25 L per 1 kg of the Compound [I]. When a formic acid-triethylamine mixture is used, the amount of use of triethylamine is usually about 0.1 to 1 mol, and preferably about 0.2 to 0.7 mol per 1 mol of formic acid.

The asymmetric transfer hydrogenation can be suitably performed by adding and dissolving the iridium(III) complex having a chiral prolinamide compound as a ligand in the solution of the Compound [I] under inert gas atmosphere, and then adding the hydrogen donor compound dropwise to the mixture. This reaction is suitably performed at −70° C. to the reflux temperature of the solvent, and preferably at about −10 to 30° C. The reaction is usually completed in 5 minutes to 2 hours. In order to raise the stability of the imine compound, the reaction may also be performed in the presence of a dehydrating agent such as anhydrous magnesium sulfate, anhydrous calcium sulfate, molecular sieves and orthoformic acid esters.

An example of the above asymmetric transfer hydrogenation is the reaction illustrated by the following reaction formula.

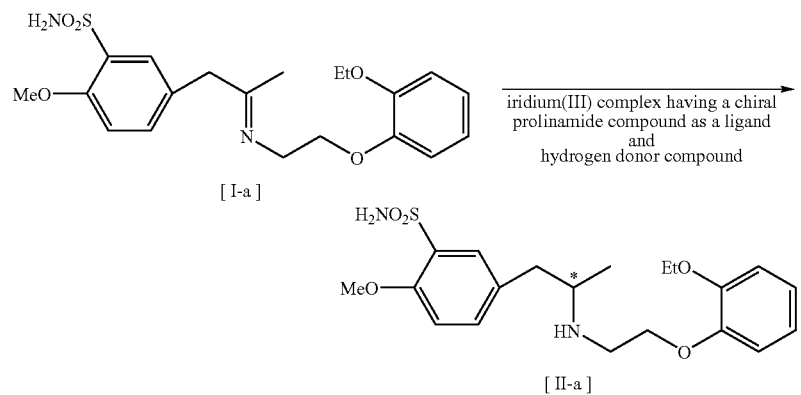

-continued

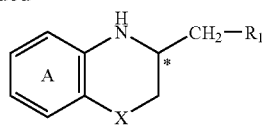

(wherein each symbol has the same meaning as defined above.)

Compound [III]+Compound [IV]+Compound [V]→Compound [VI]→Compound [VII]

Chiral amines can also be produced in an excellent manner in terms of chemical selectivity by another method, i.e., asymmetric transfer hydrogenation via a production step of a metal-containing aminoalcohol compound from ketone and amine. Namely, a chiral amine represented by the general formula [VII] (hereinafter sometimes referred to just as the Compound [VII]) can be produced by reacting an amine represented by the general formula [III] (hereinafter sometimes referred to just as the Compound [III]) and a ketone represented by the general formula [IV] (hereinafter sometimes referred to just as the Compound [IV]), in the presence of a metal compound represented by the general formula [V] (for example, Lewis acids such as titanium tetraisopropoxide) (hereinafter sometimes referred to just as the Compound [V]) to give a metal-containing aminoalcohol compound represented by the general formula [VI] (hereinafter sometimes referred to just as the Compound [VI]), and then subjecting the metal-containing aminoalcohol compound to the reaction in the presence of the above-mentioned hydrogen donor compound and the above-mentioned iridium(III) complex having a chiral prolinamide compound as a ligand.

In general, when a mixture of ketone and amine is subjected to reductive amination in the presence of the above-mentioned catalyst and the above-mentioned hydrogen donor compound, the main product is an alcohol compound resulting from simple reduction of the ketone. By interposing the production step of a metal-containing aminoalcohol compound, undesired alcohol production can be reduced to zero or a trace level.

In the Compound [III], the "alkyl" moiety in the optionally substituted alkyl group represented by $R_4$ or $R_5$ is preferably a straight or branched alkyl group having 1 to 20 carbon atoms. Examples thereof include methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl and oxadecyl. The "aryl" moiety in the optionally substituted aryl group represented by $R_4$ or $R_5$ is preferably an aromatic hydrocarbon group having 6 to 14 carbon atoms. Examples thereof include phenyl, naphthyl and anthranil. Examples of the "aralkyl" moiety in the optionally substituted aralkyl group represented by $R_4$ or $R_5$ include alkyl groups having 1 to 3 carbon atoms and being substituted by the above-mentioned "aryl" moiety, more specifically, benzyl, phenylethyl, phenylpropyl and naphthylmethyl, for example. Examples of the "heteroaryl" moiety in the optionally substituted heteroaryl group represented by $R_4$ or $R_5$ include furyl, thienyl, oxazolyl, isoxazolyl, thiazolyl, isothiazolyl, pyrrolyl, imidazolyl, pyrazolyl, pyridyl, pyrimidinyl, pyrazinyl, phthalazinyl, triazinyl, indolyl, isoindolyl, quinolinyl, isoquinolinyl and dibenzofuranyl. The "cycloalkyl" moiety in the optionally substituted cycloalkyl group represented by $R_4$ or $R_5$ is preferably a cycloalkyl group having 3 to 7 carbon atoms. Examples thereof include cyclopropyl, cyclobutyl, cyclopentyl, cyclohexyl and cycloheptyl. Examples of a substituent in the above "alkyl", "aryl", "aralkyl", "heteroaryl" and "cycloalkyl" moieties are the same as those of the substituent (A) described above.

In the Compound [IV], the "alkyl" moiety in the optionally substituted alkyl group represented by $R_6$ or $R_7$ is preferably a straight or branched alkyl group having 1 to 20 carbon atoms. Examples thereof include methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl and oxadecyl. The "aryl" moiety in the optionally substituted aryl group represented by $R_6$ or $R_7$ is preferably an aromatic hydrocarbon group having 6 to 14 carbon atoms. Examples thereof include phenyl, naphthyl and anthranil. Examples of the "aralkyl" moiety in the optionally substituted aralkyl group (=aryl alkyl group) represented by $R_6$ or $R_7$ include alkyl groups having 1 to 3 carbon atoms and being substituted by the above-mentioned "aryl" moiety, more specifically, benzyl, phenylethyl, phenylpropyl and naphthylmethyl, for example. Examples of the "heteroaryl" moiety in the optionally substituted heteroaryl group represented by $R_6$ or $R_7$ include furyl, thienyl, oxazolyl, isoxazolyl, thiazolyl, isothiazolyl, pyrrolyl, imidazolyl, pyrazolyl, pyridyl, pyrimidinyl, pyrazinyl, phthalazinyl, triazinyl, indolyl, isoindolyl, quinolinyl, isoquinolinyl and dibenzofuranyl. The "cycloalkyl" moiety in the optionally substituted cycloalkyl group represented by $R_7$ is preferably a cycloalkyl group having 3 to 7 carbon atoms. Examples thereof include cyclopropyl, cyclobutyl, cyclopentyl, cyclohexyl and cycloheptyl. Examples of the esterified carboxyl group represented by $R_6$ or $R_7$ include alkoxycarbonyl groups (for example, methoxycarbonyl etc.) and aryloxycarbonyl groups (for example, phenoxycarbonyl etc.). Examples of a substituent in the above "alkyl", "aryl", "aralkyl", "heteroaryl" and "cycloalkyl" moieties are the same as those of the substituent (A) described above.

In the Compound [V], the alkoxy group represented by X is preferably a straight or branched alkoxy group having 1 to 6 carbon atoms. Examples thereof include methoxy, ethoxy, propoxy and isopropoxy. The aryloxy group represented by X is, for example, phenoxy etc. The acyloxy group represented by X is, for example, acetoxy etc. The halogen represented by X has the same meaning as defined above. Preferable examples of the Compound [V] include boron trifluoride, zinc trifluoromethanesulfonate, aluminum triethoxide, zirconium tetrapropoxide, titanium tetraethoxide and titanium tetraisopropoxide. Titanium tetraisopropoxide is especially preferred.

The Compound [VI] can be easily produced only by adding the Compound [V] to a mixture of the Compound [III] and the Compound [IV] in the presence or absence of a solvent under inert gas atmosphere, and then stirring at room temperature for tens of minutes to several hours. The amount of use of the Compound [III] is usually about 1 to 20 mol, and preferably about 3 to 10 mol per 1 mol of the Compound [IV]. The amount of use of the Compound [V] is usually about 1 to 5 mol, and preferably about 1 to 3 mol per 1 mol of the Compound [IV]. The solvent is preferably acetonitrile, N,N-dimethylformamide, tetrahydrofuran, dimethoxyethane, dichloromethane or the like. The amount of use of the solvent is usually 1 to 50 L, and preferably 2 to 25 L per 1 kg of the Compound [IV].

After the Compound [VI] is produced, the iridium(III) complex having a chiral prolinamide compound as a ligand, and the hydrogen donor compound are successively added thereto for asymmetric transfer hydrogenation. Thus, the Compound [VII] can be easily produced. The amount of use of the iridium(III) complex having a chiral prolinamide compound as a ligand is usually about 0.1 to 10 mol %, and preferably about 0.2 to 2 mol % relative to the Compound [IV] in the case where the complex is a dimer. The amount of use of the hydrogen donor compound is usually about 1 to 20 mol, and preferably about 3 to 10 mol per 1 mol of the Compound [IV]. The solvent is preferably acetonitrile, N,N-dimethylformamide, tetrahydrofuran, dimethoxyethane, dichloromethane or the like. The amount of use of the solvent is usually 1 to 50 L, and preferably 2 to 25 L per 1 kg of the Compound [IV].

In the case where the Compound [III] in this reaction route is ammonia, the compound may also be used in the form of ammonium formate to serve as the hydrogen donor compound as well. In this case, the reaction can be performed by adding ammonium formate to the Compound [IV] and the Compound [V], and then adding thereto the iridium(III) complex having a chiral prolinamide compound as a ligand. The amount of use of the ammonium formate is usually about 1 to 20 mol, and preferably about 3 to 10 mol per 1 mol of the Compound [IV]. In either case, the reaction is suitably performed at −70° C. to the reflux temperature of the solvent, and preferably at about −10 to 30° C. The reaction is usually completed in several to tens of hours.

After completion of the reaction, objective optically active amines can be easily obtained by ordinary treatments such as concentration, extraction, filtration and washing. If needed, crystallization and recrystallization, salt formation with an achiral acid such as hydrochloric acid, sulfuric acid and methanesulfonic acid, and subsequent recrystallization, chemical optical resolution using a chiral acid such as mandelic acid, tartaric acid, ditoluoyl tartaric acid and malic acid, or other techniques can be employed, resulting in production of optically pure chiral amines.

EXAMPLES

Hereinafter, the present invention will be illustrated in detail by way of Examples, but is not limited thereto.

Example 1

Synthesis of (S)—N-(2-methoxy-3-dibenzofuranyl)-2-pyrrolidinecarboxamide 43.1 g of N-(tert-butoxycarbonyl)-S-proline was dissolved in 500 ml of tetrahydrofuran, and to this were added successively 20.2 g of triethylamine and 21.7 g of ethyl chlorocarbonate. The mixture was stirred at −5 to 5° C. for about 30 minutes. To the mixture was added dropwise a tetrahydrofuran solution containing 42.6 g of 3-amino-2-methoxydibenzofuran at the same temperature over about 30 minutes. Then, stirring continued at 15 to 25° C. overnight for completion of the reaction. After that, the reaction mixture was concentrated in vacuo and the residue was dissolved in ethyl acetate. The mixture was washed successively with brine, a 5% aqueous solution of sodium bicarbonate and water, and then concentrated in vacuo, to give 86.2 g of (S)-1-(tert-butoxycarbonyl)-N-(2-methoxy-3-dibenzofuranyl)-2-pyrrolidinecarboxamide as a solid. 35.0 g of the obtained compound was dissolved in 100 ml of methanol. Under ice-cooling, to this was added 200 ml of 4N-hydrochloric acid/ethyl acetate and then the mixture was stirred overnight. The precipitate was collected by filtration, washed with ethyl acetate and dried, to give 23.4 g of (S)—N-(2-methoxy-3-dibenzofuranyl)-2-pyrrolidinecarboxamide hydrochloride as a white crystal. After 10.0 g of the hydrochloride was neutralized by aqueous sodium hydroxide solution, extraction with ethyl acetate, washing with water, concentration and recrystallization from ethyl acetate gave 6.9 g of the free base of the hydrochloride as a white crystal.

Melting point: 170 to 171° C.
Optical rotation: $[\alpha]_D^{20}$ −61.9° (C=0.5, MeOH)
NMR: $^1$H-NMR (200 MHz, CDCl$_3$): δ 1.67-1.88 (2H, m), 2.01-2.30 (1H, m), 2.98-3.19 (2H, m), 3.90-3.98 (1H, m), 4.01 (3H, S), 7.26-7.43 (4H, m), 7.52-7.56 (1H, m), 7.82-7.86 (1H, m), 8.79 (1H, S)

(R)—N-(2-methoxy-3-dibenzofuranyl)-2-pyrrolidinecarboxamide can be obtained by performing a series of the above procedures except that N-(tert-butoxycarbonyl)-R-proline is used instead of N-(tert-butoxycarbonyl)-S-proline.

Example 2

Synthesis of (R)-5-[2-[[2-(2-ethoxyphenoxy)ethyl]amino]propyl]-2-methoxybenzenesulfonamide (R)-mandelate (1) Preparation of (S)-chloro[(1,2,3,4-η)-pentamethyl-2,4-cyclopentadien-1-yl][N-(2-methoxy-3-dibenzofuranyl)-2-pyrrolidinecarboxamidato-κN1, κN2]iridium(III) catalyst 79.7 mg of pentamethylcyclopentadienyl iridium(III) chloride dimer, 65.2 mg of (S)—N-(2-methoxy-3-dibenzofuranyl)-2-pyrrolidinecarboxamide and 22.3 mg of triethylamine were added to 5 ml of acetonitrile. The mixture was stirred under argon atmosphere at room temperature for about 30 minutes, to give a catalyst-containing mixture.

(2) Synthesis of (R)-5-[2-[[2-(2-ethoxyphenoxy)ethyl]amino]propyl]-2-methoxybenzenesulfonamide (R)-mandelate 4.87 g of 2-methoxy-5-(2-oxopropyl)benzenesulfonamide, 3.62 g of 2-(2-ethoxyphenoxy)ethylamine and 10 mg of sodium acetate were added to 30 ml of acetonitrile. The mixture was heated while stirred under reflux for about 1 hour. Then, the solvent was evaporated off in vacuo, to give 7.84 g of an imine compound as a powder. The obtained imine compound was again dissolved in 70 ml of acetonitrile, and to this was added 1.0 g of anhydrous magnesium sulfate. The mixture was cooled to −3 to 3° C. under argon atmosphere. To this mixture was added the whole amount of the above catalyst-containing mixture, and stirring continued at the same temperature for about 30 minutes. To this was added dropwise 12.0 ml of a mixed solution of formic acid/triethylamine (molar ratio: 5/2), and then stirring further continued at the same temperature for about 5 hours. After that, the reaction mixture was gradually returned to room temperature, and stirring continued overnight for completion of the reaction. After that, the solvent was evaporated off in vacuo and the residue was dissolved in methyl isobutyl ketone. Following this, extraction with aqueous methanesulfonic acid solution was performed. After the aqueous layer was rendered weakly alkaline with aqueous sodium hydroxide solution, separated oily material was extracted with methyl ethyl ketone. The extract solution was washed with saturated brine, dried and concentrated, to give 7.96 of 5-[2-[(2-(2-ethoxyphenoxy)ethyl)amino]propyl]-2-methoxybenzenesulfonamide (crude crystal containing excess R-isomer) as a light brown powder. The obtained compound was analyzed using a chiral chromatography column (CHIRALPAK AD-H; manufactured by Daicel Chemical Industries, Ltd.) with a solvent made of n-hexane/2-propanol/diethylamine (800/200/1). The result showed that the optical purity of the R-isomer was 70.7% ee.

Then, 6.0 g of the crude crystal was dissolved in 42.0 ml of aqueous acetone containing 10% water and to this was added 3.36 g of (R)-mandelic acid. The mixture was heat-dissolved, and then allowed to stand at 15 to 25° C. overnight. The precipitate was collected by filtration, washed with acetone and dried, to give 4.56 g of (R)-tamsulosin (R)-mandelate, i.e., (R)-5-[2-[[2-(2-ethoxyphenoxy)ethyl]amino]propyl]-2-methoxybenzenesulfonamide (R)-mandelate as a colorless crystal. The optical purity of the R-isomer of the obtained compound was 97.0% ee. Moreover, recrystallization from aqueous acetone containing 10% water was performed to give 3.29 g of a purified product. The optical purity of the R-isomer of the purified product was 100% ee.

Optical rotation: $[\alpha]_D^{20}$ −31.90° (C=0.5, MeOH)
NMR: $^1$H-NMR (200 MHz, DMSO-d$_6$): δ 0.99-1.03 (3H, d), 1.23-1.30 (3H, t), 2.47-2.59 (1H, q), 2.97-3.05 (1H, q), 3.10-3.30 (1H, m), 3.14-3.20 (2H, t), 3.88 (3H, s), 3.94-4.04 (2H, q), 4.09-4.15 (2H, t), 4.43 (2H, m), 4.75 (1H, s), 6.82-7.43 (9H, m), 7.04 (2H, m), 7.58-7.60 (1H, d)

(R)—N-(2-methoxy-3-dibenzofuranyl)-2-pyrrolidinecarboxamide can be produced by the same method as (S)—N-(2-methoxy-3-dibenzofuranyl)-2-pyrrolidinecarboxamide.

(S)-5-[2-[[2-(2-ethoxyphenoxy)ethyl]amino]propyl]-2-methoxybenzenesulfonamide (S)-mandelate can be obtained by performing a series of the above procedures except that (R)—N-(2-methoxy-3-dibenzofuranyl)-2-pyrrolidinecarboxamide and (S)-mandelic acid are used instead of (S)—N-(2-methoxy-3-dibenzofuranyl)-2-pyrrolidinecarboxamide and (R)-mandelic acid.

Example 3

Synthesis of (R)-1-(4-methoxyphenyl)-2-benzylaminopropane (1) Preparation of (R)-chloro[(1,2,3,4-η)-pentamethyl-2,4-cyclopentadien-1-yl](N-6-quinolinyl-2-pyrrolidinecarboxamidato-κN1,κN2)iridium(III) catalyst 398 mg of pentamethylcyclopentadienyl iridium(III) chloride dimer, 253 mg of (S)—N-6-quinolinyl-2-pyrrolidinecarboxamide and 111 mg of triethylamine were added to 20 ml of acetonitrile. The mixture was stirred under argon atmosphere at room temperature for about 30 minutes, to give a catalyst-containing mixture.

(2) Synthesis of (R)-1-(4-methoxyphenyl)-2-benzylaminopropane methanesulfonate 8.21 g of 4-methoxyphenyl acetone and 5.36 g of benzylamine were dissolved in 50 ml of toluene, and to this was added 50 mg of p-toluenesulfonic acid. The mixture was then dehydrated under reflux for 2 hours. The reaction mixture was concentrated in vacuo, to give 12.34 g of an imine compound as a light brown oily material. The obtained imine compound was again dissolved in 100 ml of acetonitrile, and to this was added 5.0 g of anhydrous magnesium sulfate. The mixture was cooled to −3 to 3° C. under argon atmosphere.

To this mixture was added the whole amount of the above catalyst-containing mixture, and stirring continued at the same temperature for about 30 minutes. To this was added dropwise 30.0 ml of a mixed solution of formic acid/triethylamine (molar ratio: 5/2), and then stirring further continued at the same temperature for about 5 hours. After that, the reaction mixture was gradually returned to room temperature, and stirring continued overnight for completion of the reaction. After that, the solvent was evaporated off in vacuo and the residue was treated with aqueous methanesulfonic acid solution and diisopropyl ether. After the aqueous layer was rendered weakly alkaline with aqueous sodium hydroxide solution, extraction with ethyl acetate was performed. The extract solution was washed with brine, dried and concentrated, to give 10.66 g of an oily material. The obtained oily material was analyzed using a chiral chromatography column (CHIRALCEL OD; manufactured by Daicel Chemical Industries, Ltd.) with a solvent made of n-hexane/2-propanol/acetic acid/trifluoroacetic acid (950/50/1/1). The result showed that the optical purity was 83.2% ee. Then, 9.00 g of the oily material was dissolved in 80 ml of acetonitrile. The mixture was heated to 50° C. and 4.07 g of methanesulfonic acid was gradually added thereto, resulting in crystal precipitation. After the reaction mixture was cooled to room temperature, the precipitate was collected by filtration, washed with acetonitrile and dried, to give 8.67 g of a slightly yellowish white crystal. Moreover, recrystallization from a solvent made of methanol was performed to give 5.05 g of the title compound as a colorless crystal. After this methanesulfonate was neutralized, the optical purity of the resulting free base was 100% ee.

Melting point: 201 to 203° C.

Optical rotation: $[\alpha]_D^{20}$ −16.6° (C=1.0, MeOH)

NMR: $^1$H-NMR (200 MHz, CDCl$_3$): δ 1.26-1.29 (3H, d), 2.68 (3H, S), 3.29-3.32 (2H, m), 3.44-3.54 (1H, m), 3.77 (3H, S), 4.21-4.27 (1H, d), 4.28-4.35 (1H, d), 6.87-6.94 (2H, d), 7.13-7.21 (2H, d), 7.43-7.55 (5H, m)

(S)-1-(4-methoxyphenyl)-2-benzylaminopropane methanesulfonate can be obtained by performing a series of the above procedures except that (R)—N-6-quinolinyl-2-pyrrolidinecarboxamide is used instead of (S)—N-6-quinolinyl-2-pyrrolidinecarboxamide.

Example 4

Synthesis of (R)-1-(4-methoxyphenyl)-2-ethylaminopropane (1) Preparation of (S)-chloro[(1,2,3,4-η)-pentamethyl-2,4-cyclopentadien-1-yl](2-pyrrolidinecarboxamidato-κN1,κN2)iridium(III) catalyst 239 mg of pentamethylcyclopentadienyl iridium(III) chloride dimer, 72 mg of (S)-prolinamide and 67 mg of triethylamine were added to 5 ml of acetonitrile. The mixture was stirred under argon atmosphere at room temperature for about 30 minutes, to give a catalyst-containing mixture.

(2) Synthesis of (R)-1-(4-methoxyphenyl)-2-ethylaminopropane 4.10 g of 4-methoxyphenyl acetone and 10.2 g of ethylamine hydrochloride were added to 70 ml of acetonitrile, and to this was further added 12.6 g of triethylamine. The mixture was stirred in a sealed tube at room temperature overnight. After 14.2 g of titanium tetraisopropoxide was added to the reaction mixture, and stirring continued at room temperature for about 1 hour, the absorption peak corresponding to ketone disappeared in the IR spectrum. The reaction mixture was cooled to −3 to 3° C. under argon atmosphere.

To this reaction mixture were added the whole amount of the above catalyst-containing mixture and 5.18 g of formic acid, and stirring continued at the same temperature for about 5 hours. Then, the reaction mixture was gradually returned to room temperature, and stirring continued overnight. After completion of the reaction, the solvent was evaporated off in vacuo and the residue was treated with dilute hydrochloric acid and ethyl acetate. The acidic aqueous layer was rendered weakly alkaline with aqueous sodium hydroxide solution. To this was added ethyl acetate and stirring was performed for a short time. Then, the reaction mixture was filtered by aspiration to remove insoluble matter, and the insoluble matter was washed with ethyl acetate. The organic layer of the filtrate was separated, washed with brine, dried and concentrated, to give 4.98 g of an oily material. The oily material did not contain alcohol resulting from simple reduction of 4-methoxyphenyl acetone, and the optical purity of the objective amine was 51.9% ee. Then, 9.09 g of di-p-toluoyl-L-tartaric acid was added to 4.50 g of the oily material, and the mixture was heat-dissolved in 200 ml of a mixed solvent of ethanol/methanol (1/1). After that, the mixture was cooled to room temperature. The precipitate was collected by filtration, washed with ethanol and dried, to give 8.03 g of a crystal (optical purity: 93.3% ee). The obtained crystal was subjected to recrystallization from ethanol/methanol (1/1), to give 5.30 g of a colorless crystal (optical purity: 98.2% ee). After the di-p-toluoyl-L-tartrate was neutralized with aqueous sodium hydroxide solution, extraction with ethyl acetate and subsequent concentration gave 2.00 g of the title compound as an oily material.

Optical rotation: $[\alpha]_D^{20}$ −25.4° (C=0.5, MeOH)

NMR: $^1$H-NMR (200 MHz, CDCl$_3$): δ 1.02-1.09 (3H, t), 1.03-1.06 (2H, d), 2.48-2.80 (4H, m), 2.81-2.91 (1H, m), 3.79 (3H, s), 6.84 (2H, d), 7.10 (2H, d)

(S)-1-(4-methoxyphenyl)-2-ethylaminopropane can be obtained by performing a series of the above procedures except that (R)-prolinamide is used instead of (S)-prolinamide.

Example 5

Synthesis of (3S)-7,8-difluoro-3-methyl-2,3-dihydro-4H-1,4-benzoxazine (1) Preparation of (S)-chloro[(1,2,3,4-η)-pentamethyl-2,4-cyclopentadien-1-yl](2-pyrrolidinecarboxamidato-κN1,κN2)iridium(III) catalyst 637 mg of pentamethylcyclopentadienyl iridium(III) chloride dimer, 192 mg of (S)-prolinamide and 356 mg of triethylamine were added to 20 ml of dichloromethane. The mixture was stirred at room temperature for about 30 minutes, to give a catalyst-containing mixture.

(2) Synthesis of (3S)-7,8-difluoro-3-methyl-2,3-dihydro-4H-1,4-benzoxazine 7.29 g of 7,8-difluoro-3-methyl-2H-1,4-benzoxazine was dissolved in 125 ml of dichloromethane. The mixture was stirred under nitrogen stream and then cooled to −35 to −30° C.

To this mixture was added the whole amount of the above catalyst-containing mixture, and stirring continued at the same temperature for about 30 minutes. To this was added dropwise 30.0 ml of a mixed solution of formic acid/triethylamine (molar ratio: 5/2), and then stirring further continued at the same temperature for 8 hours until completion of the reaction. After the reaction mixture was rendered alkaline with aqueous sodium hydroxide solution, the organic layer was separated, washed with water and concentrated, to give 7.54 g of an oily material.

This material was subjected to purification using column chromatography on silica gel. The fraction eluted by dichloromethane/n-hexane (1/1) was concentrated to give 5.12 g of 7,8-difluoro-3-methyl-2,3-dihydro-4H-1,4-benzoxazine (product containing excess S-isomer) as an oily material. The obtained compound was analyzed using a chiral chromatography column (CHIRALPAK IB; manufactured by Daicel Chemical Industries, Ltd.) with a mobile phase made of n-hexane/methanol/diethylamine (1000/1/1). The result showed that the optical purity of the S-isomer was 93.2% ee.

NMR: $^1$H-NMR (200 MHz, CDCl$_3$): δ 1.19 (3H, d), 3.43-3.58 (1H, m), 3.78 (1H, dd), 4.28 (1H, dd), 6.21-6.31 (1H, m), 6.48-6.62 (1H, m)

Example 6

Synthesis of 2,3-dihydro-1-[3-(phenylmethoxy)propyl]-5-[(2R)-2-[[2-[2-(2,2,2-trifluoroethoxy)phenoxy]ethyl]amino]propyl]-1H-indole-7-carbonitrile (1) 8.85 g of 1-[3-(benzyloxy)propyl]-2,3-dihydro-5-(2-oxopropyl)-1H-indole-7-carbonitrile and 6.25 g of 2-[2-(2,2,2-trifluoroethoxy)phenoxy]-ethanamine were dissolved in 70 ml of toluene, and to this was added 10 mg of p-toluenesulfonic acid. The mixture was then dehydrated under reflux while stirred for 1 hour. After that, the solvent was evaporated off in vacuo, to give 14.34 g of an imine compound as an oily material.

(2) Preparation of (S)-chloro[(1,2,3,4-η)-pentamethyl-2,4-cyclopentadien-1-yl](2-pyrrolidinecarboxamidato-κN1,κN2)iridium(III) catalyst 498 mg of pentamethylcyclopentadienyl iridium(III) chloride dimer, 150 mg of (S)-prolinamide and 278 mg of triethylamine were added to 20 ml of dichloromethane. The mixture was stirred at room temperature for about 30 minutes, to give a catalyst-containing mixture.

(3) Synthesis of 2,3-dihydro-1-[3-(phenylmethoxy)propyl]-5-[(2R)-2-[[2-[2-(2,2,2-trifluoroethoxy)phenoxy]ethyl]amino]propyl]-1H-indole-7-carbonitrile 14.10 g of the above imine compound was dissolved in 125 ml of dichloromethane. The mixture was stirred under nitrogen stream and then cooled to 0 to 5° C.

To this mixture was added the whole amount of the above catalyst-containing mixture, and stirring continued at the same temperature for about 30 minutes. To this was added dropwise 16.5 ml of a mixed solution of formic acid/triethylamine (molar ratio: 5/2), and then stirring further continued at the same temperature for about 5 hours. After that, the reaction mixture was gradually returned to room temperature, and stirring continued overnight. After completion of the reaction, the reaction mixture was rendered alkaline with aqueous potassium carbonate solution, and the organic layer was separated, washed with water and concentrated, to give 14.75 g of an oily material.

This material was subjected to purification using column chromatography on silica gel. The fraction eluted by dichloromethane/acetone (5/1) was concentrated to give 8.01 g of 2,3-dihydro-1-[3-(phenylmethoxy)propyl]-5-[(2R)-2-[[2-[2-(2,2,2-trifluoroethoxy)phenoxy]ethyl]amino]propyl]-1H-indole-7-carbonitrile (product containing excess R-isomer) as an oily material. The obtained compound was analyzed using a chiral chromatography column (CHIRALPAK AD-H; manufactured by Daicel Chemical Industries, Ltd.) with a mobile phase made of n-hexane/2-propanol/diethylamine (800/100/1). The result showed that the optical purity of the R-isomer was 80.1% ee.

NMR: $^1$H-NMR (200 MHz, CDCl$_3$): δ 1.05 (3H, d), 1.90-2.00 (2H, m), 2.35-2.45 (1H, m), 2.55-2.65 (1H, m), 2.85-2.95 (3H, m), 2.95-3.10 (2H, m), 3.54 (2H, t), 3.60-3.70 (4H, m), 4.05-4.15 (2H, m), 4.25-4.35 (2H, m), 4.52 (2H, s), 6.85-7.10 (6H, m), 7.25-7.35 (5H, m)

Further purification can be performed by subjecting the above oily material with the optical purity of 80.1% ee to crystallization from a solvent made of ethanol, and isolating the resulting crystal in the form of D-(−)-tartrate. The optical purity of the thus-obtained 2,3-dihydro-1-[3-(phenylmethoxy)propyl]-5-[(2R)-2-[[2-[2-(2,2,2-trifluoroethoxy)phenoxy]ethyl]amino]propyl]-1H-indole-7-carbonitrile D-(−)-tartrate was 99.6% de, which was higher compared with that before crystallization, and the specific rotation thereof was $[\alpha]_D^{25}$ −7.6° (C=0.99, MeOH).

Reference Example

Synthesis of 1-[3-(phenylmethoxy)propyl]-2,3-dihydro-5-(2-oxopropyl)-1H-indole-7-carbonitrile 19.80 g of 5-bromoindoline was dissolved in 250 ml of toluene, and to this was added dropwise 110 ml of dichloromethane solution of boron trichloride (1.0M) with stirring under ice-cooling.

Dichloromethane was evaporated off with gradual rise in temperature. The reaction mixture was stirred at 110° C. for 1 hour and then cooled to room temperature. To this was added 10.0 ml of methyl thiocyanate, and stirring continued at room temperature overnight. After completion of the reaction, the solvent was evaporated off in vacuo and the resulting residue was dissolved in 250 ml of methanol. To this was added a solution of 56.0 g of sodium hydroxide in 100 ml of water, and the mixture was stirred at 50 to 60° C. for 5 hours. After the reaction mixture was cooled and then acidified with hydrochloric acid, extraction with ethyl acetate, washing with water and concentration gave 14.20 g of 5-bromo-7-indolinecarbonitrile as a light brown powder.

NMR: $^1$H-NMR (200 MHz, CDCl$_3$): δ 3.12 (2H, t), 3.73 (2H, t), 7.22-7.30 (2H, m)

10.00 g of 5-bromo-7-indolinecarbonitrile was dissolved in 120 ml of dimethylformamide. The mixture was cooled to 0° C. under nitrogen atmosphere, and to this was added 2.37 g of 60% sodium hydride.

After 30-minute stirring, 11.32 g of 3-bromopropyl benzyl ether was added to the reaction mixture, and stirring further continued at the same temperature for 7 hours until completion of the reaction.

The reaction mixture was poured into water and extraction with ethyl acetate was performed. The extract solution was washed with water and concentrated, and the resulting residue was subjected to purification using column chromatography on silica gel. The fraction eluted by n-hexane/diisopropyl ether (3/1) was concentrated to give 13.45 g of 1-[3-(benzyloxy)propyl]-2,3-dihydro-5-bromo-1H-indole-7-carbonitrile as an oily material.

NMR: $^1$H-NMR (200 MHz, CDCl$_3$): δ 1.90-2.03 (2H, m), 2.95 (2H, t), 3.54-3.72 (7H, m), 4.51 (2H, s), 7.09 (1H, m), 7.20 (1H, m), 7.30-7.36 (5H, m)

13.37 g of 1-[3-(benzyloxy)propyl]-2,3-dihydro-5-bromo-1H-indole-7-carbonitrile, 23.11 g of tri-n-butyltin methoxide and 7.20 g of isopropenyl acetate were dissolved in 270 ml of toluene, and stirring continued under nitrogen atmosphere at room temperature for 1 hour.

To this were added 0.33 g of tris(dibenzylideneacetone)dipalladium(0) and 0.57 g of 2-dicyclohexylphosphino-2'-(dimethylamino)biphenyl, and stirring continued at 75 to 85° C. for 1.5 hours until completion of the reaction.

The solvent was evaporated off in vacuo, and the resulting residue was subjected to purification using column chromatography on silica gel. The fraction eluted by n-hexane/ethyl acetate (4/1) was concentrated to give 11.11 g of 1-[3-(benzyloxy)propyl]-2,3-dihydro-5-(2-oxopropyl)-1H-indole-7-carbonitrile as an oily material.

NMR: $^1$H-NMR (200 MHz, CDCl$_3$): δ 1.91-2.06 (2H, m), 2.17 (3H, s), 2.94 (2H, t), 3.51 (2H, s), 3.54-3.72 (6H, m), 4.52 (2H, s), 6.94 (2H, m), 7.29-7.38 (5H, m)

INDUSTRIAL APPLICABILITY

According to the present invention, chiral amines, which are compounds of immense importance in the fields of pharmaceuticals, fine chemicals and the like, can be produced in a simple and high-yield manner.

The invention claimed is:

1. A method for producing a chiral amine represented by the formula [II]:

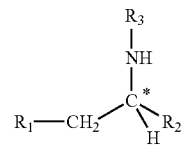

[II]

wherein $R_1$ represents a hydrogen atom, an optionally substituted alkyl group, an optionally substituted aryl group, an optionally substituted aralkyl group, an optionally substituted cycloalkyl group or an optionally substituted heteroaryl group, and $R_2$ represents an optionally substituted alkyl group, an optionally substituted aralkyl group, an optionally substituted cycloalkyl group, a carboxyl group, an esterified carboxyl group, a cyano group or an amide group, or $R_1$ and $R_2$ together with the adjacent carbon atoms may form a ring by binding to each other at the ends thereof;

$R_3$ represents a hydrogen atom, an optionally substituted alkyl group, an optionally substituted aryl group, an optionally substituted aralkyl group, an optionally substituted heteroaryl group or an optionally substituted cycloalkyl group, or $R_2$ and $R_3$ together with the adjacent group —NH—C— may form a nitrogen containing heterocycle optionally having a substituent; and the symbol "*" represents a chiral carbon atom, comprising subjecting an imine compound represented by the formula [I]:

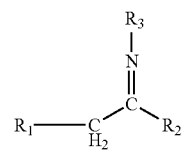

[I]

wherein $R_1$, $R_2$ and $R_3$ have the same meanings as defined above, or $R_2$ and $R_3$ together with the adjacent group —N=C— may form a nitrogen containing heterocycle optionally having a substituent, to asymmetric transfer hydrogenation in the presence of formic acid, and an iridium(III) complex having a chiral prolinamide compound represented by the formula [VIII]:

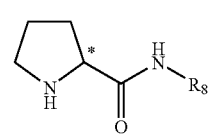

[VIII]

wherein $R_8$ represents a hydrogen atom or a heteroaryl group which may optionally be substituted, and the symbol "*" represents a chiral carbon atom, as a ligand.

2. A method for producing a chiral amine represented by the formula [VII]:

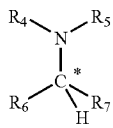

[VII]

wherein $R_4$ and $R_5$ independently represent a hydrogen atom, an optionally substituted alkyl group, an optionally substituted aryl group, an optionally substituted aralkyl group, an optionally substituted heteroaryl group or an optionally substituted cycloalkyl group, or $R_4$ and $R_5$ together with the adjacent nitrogen atom may form a ring by binding to each other at the ends thereof;

$R_6$, which is different from $R_7$, represents an optionally substituted alkyl group, an optionally substituted aryl group, an optionally substituted aralkyl group, an optionally substituted cycloalkyl group or an optionally substituted heteroaryl group, and $R_7$ represents an optionally substituted alkyl group, an optionally substituted aryl group, an optionally substituted aralkyl group, an optionally substituted heteroaryl group, an optionally substituted cycloalkyl group, a carboxyl group, an esterified carboxyl group, a cyano group or an amide group, or $R_6$ and $R_7$ together with the adjacent carbon atom may form a ring by binding to each other at the ends thereof; and the symbol "*" represents a chiral carbon atom, comprising reacting an amine represented by the formula [III]:

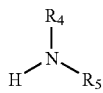

[III]

wherein $R_4$ and $R_5$ have the same meanings as defined above and a ketone represented by the formula [IV]:

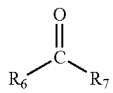

[IV]

wherein $R_6$ and $R_7$ have the same meanings as defined above, with titanium tetraisopropoxide, to produce a metal-containing aminoalcohol compound represented by the formula [VI]:

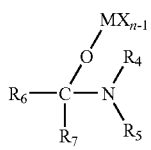

[VI]

wherein $R_4$, $R_5$, $R_6$, $R_7$, M, n and X have the same meanings as defined above, and then subjecting the metal-containing aminoalcohol compound to asymmetric transfer hydrogenation in the presence of formic acid and an iridium(III) complex having a chiral prolinamide compound represented by the formula [VIII]

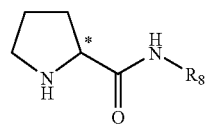

[VIII]

wherein $R_8$ represents a hydrogen atom or a heteroaryl group which may optionally be substituted, and the symbol "*" represents a chiral carbon atom, as a ligand.

3. The method according to claim 1, wherein the chiral prolinamide compound is a compound represented by the formula [VIII]:

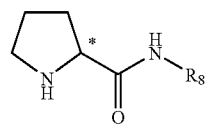

[VIII]

wherein $R_8$ represents a hydrogen atom, or a heteroaryl group selected from the group consisting of furyl, thienyl, oxazolyl, isoxazolyl, thiazolyl, isothiazolyl, pyrrolyl, imidazolyl, pyrazolyl, pyridyl, pyrimidinyl, pyrazinyl, phthalazinyl, triazinyl, indolyl, isoindolyl, quinolinyl, isoquinolinyl and dibenzofuranyl, which may optionally be substituted by (1) halogens, (2) straight or branched alkyl groups having 1 to 6 carbon atoms, (3) aralkyl groups having 5 to 12 carbon atoms, (4) straight or branched alkoxy groups having 1 to 6 carbon atoms, (5) alkyl halide groups, (6) alkoxy halide groups, (7) a hydroxyl group, (8) a mercapto group, (9) a nitro group, (10) a nitrile group or (11) an alkoxycarbonyl group, and the symbol "*" represents a chiral carbon atom.

4. The method according to claim 3, wherein $R_8$ is hydrogen, 6-quinolinyl or 2-methoxy-3-dibenzofuranyl.

5. The method according to claim 1, wherein the iridium (III) complex having a chiral prolinamide compound as a ligand is an (S)- or (R)-chloro[(1,2,3,4-η)-pentamethyl-2,4-cyclopentadien-1-yl][N-(2-methoxy-3-dibenzofuranyl)-2-pyrrolidinecarboxamidato-κN1,κN2]iridium(III) catalyst, an (S)- or (R)-chloro[(1,2,3,4-η)-pentamethyl-2,4-cyclopentadien-1-yl](N-6-quinolinyl-2-pyrrolidinecarboxamidato-κN1,κN2)iridium(III) catalyst, or an (S)- or (R)-chloro[(1,2,3,4-η)-pentamethyl-2,4-cyclopentadien-1-yl](2-pyrrolidinecarboxamidato-κN1,κN2)iridium(III) catalyst.

6. A method for producing tamuslosin represented by the formula [II-a]:

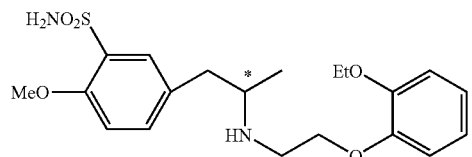

[II-a]

wherein Me represents a methyl group, Et represents an ethyl group, and the symbol "*" represents a chiral carbon atom, or an acid addition salt thereof,
comprising subjecting an imine compound represented by the formula [I-a]:

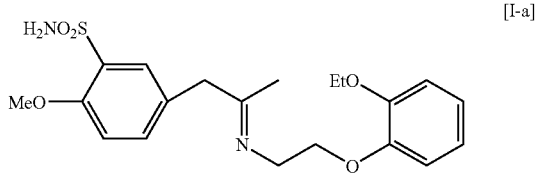

wherein Me and Et have the same meanings as defined above,
to asymmetric transfer hydrogenation in the presence of formic acid and an iridium(III) complex selected from the group consisting of (1) an (S)- or (R)-chloro[(1, 2, 3, 4-η)-pentamethyl-2,4-cyclopentadien-1-yl][N-(2-methoxy-3-dibenzofuranyl)-2-pyrrolidinecarboxamidato-kN1,kN2]iridium (III) catalyst, (2) an (S)- or (R)-chloro[(1,2,3,4-η)-pentamethyl-2,4-cyclopentadien-1-yl](N-6-quinolinyl-2-pyrrolidine-carboxamidato-kN1,kN2) iridium(III) catalyst, and (3) an (S)- or (R)-chloro[(1, 2, 3, 4-η)-pentamethyl-2,4-cyclopentadien-1-yl](2-pyrrolidinecarboxamidato-kN1,kN2) iridium(III) catalyst, and if desired, converting the resulting product into an acid addition salt thereof.

7. (S)—N-(2-methoxy-3-dibenzofuranyl)-2-pyrrolidinecarboxamide or (R)—N-(2-methoxy-3-dibenzofuranyl)-2-pyrrolidinecarboxamide.

* * * * *